United States Patent
Fu et al.

(10) Patent No.: US 10,214,556 B2
(45) Date of Patent: Feb. 26, 2019

(54) METHOD FOR PURIFYING REDUCED FORM OF β-NICOTINAMIDE ADENINE DINUCLEOTIDE

(71) Applicant: BONTAC BIO-ENGINEERING (SHENZHEN) CO., LTD, Shenzhen (CN)

(72) Inventors: Rongzhao Fu, Shenzhen (CN); Zhu Dai, Shenzhen (CN); Qi Zhang, Shenzhen (CN)

(73) Assignee: BONTAC BIO-ENGINEERING (SHENZHEN) CO., LTD, Shenzhen (CN)

( * ) Notice: Subject to any disclaimer, the term of this patent is extended or adjusted under 35 U.S.C. 154(b) by 184 days.

(21) Appl. No.: 15/109,956

(22) PCT Filed: Dec. 4, 2015

(86) PCT No.: PCT/CN2015/096403
§ 371 (c)(1),
(2) Date: Jul. 6, 2016

(87) PCT Pub. No.: WO2016/091121
PCT Pub. Date: Jun. 16, 2016

(65) Prior Publication Data
US 2016/0340381 A1  Nov. 24, 2016

(30) Foreign Application Priority Data
May 19, 2015  (CN) .......................... 2015 1 0255187

(51) Int. Cl.
*C07H 1/06*  (2006.01)
*C07H 19/207*  (2006.01)

(52) U.S. Cl.
CPC ............. *C07H 19/207* (2013.01); *C07H 1/06* (2013.01)

(58) Field of Classification Search
CPC ................................ C07H 1/06; C07H 19/207
See application file for complete search history.

(56) References Cited

U.S. PATENT DOCUMENTS 4,622,294 A  *  11/1986  Kung .................. G01N 33/532
                                                    435/14
4,783,400 A  *  11/1988  Canova-Davis ..... G01N 33/532
                                                    435/14

FOREIGN PATENT DOCUMENTS

| CN | 1586502 | 3/2005 |
| CN | 101023968 | 8/2007 |
| CN | 104898710 | 9/2015 |

OTHER PUBLICATIONS (R) Ryll et al., Improved Ion-Pair High-Performance Liquid Chromatographic Method for the Quantification of a Wide Variety of Nucleotides and Sugar-Nucleotides in Animal Cells, J. of Chromatography, Biomedical Sciences and Applications, 570(1), 77-88 (1991), only abstract upplied.*
International Search Report for International Application No. PCT/CN2015/096403, dated Mar. 9, 2016, with English translation, total 5 pages.
Wen, Juyi et al., "Study on the Isolation and Purification of NADH by Muti-ultrafiltration and Affinity Ultrafiltration", Chinese Journal of Pharmaceutical Biotechnology, vol. 12, No. 5, Dec. 31, 2005, cited in the International Search Report and English abstract provided, total 6 pages.
Lluis et al. "Kinetic formulations for the oxidation and the reduction of glyoxylate by lactate dehydrogenase", Biochimica et Biophysica Acta, Feb. 9, 1977, 480(2), pp. 333-342, 10 pages.

* cited by examiner

*Primary Examiner* — Lawrence E Crane
(74) *Attorney, Agent, or Firm* — Hamre, Schumann, Mueller & Larson, P.C.

(57) ABSTRACT

A method for purifying a salt of reduced form of β-nicotinamide adenine dinucleotide (NADH) includes: sequentially microfiltrating and nanofiltrating a reaction solution obtained after an enzymatic reaction, collecting a concentrate for use; adding an ion pair reagent to the concentrate, and purifying by gradient elution to obtain a purified filtrate using a reverse-phase chromatographic column as a stationary phase, a buffer solution as a phase A, and ethanol as a phase B; changing the cations in the purified filtrate into sodium ions to obtain a filtrate by using a cation exchange resin; and nanofiltrating the filtrate, and freeze drying in a vacuum freeze drier. The method results in an excellent purity and yield of a salt of NADH that meets requirements in industry.

10 Claims, No Drawings

METHOD FOR PURIFYING REDUCED FORM OF β-NICOTINAMIDE ADENINE DINUCLEOTIDE

BACKGROUND

Technical Field

The present invention relates to a method for purifying a coenzyme, and particularly to a method for purifying reduced form of β-nicotinamide adenine dinucleotide.

Related Art

Reduced form of β-nicotinamide adenine dinucleotide is a reduced coenzyme I, which is also known as β-Nicotinamide adenine dinucleotide, reduced form, generally exists as a disodium salt, and referred to as NADH hereinafter. NADH is produced during the glycolysis and the citric acid cycle of respiration in organisms. A large amount of ATP is produced through the oxidation of NADH via transfer of 1 electron, thus meeting the energy demand in the organisms. Reduced form of β-nicotinamide adenine dinucleotide may be used in a redox reaction, to realize the transfer of electrons. Therefore, NADH is widely used in the catalysis of chemical reactions, production of raw drugs, and in the industries of healthcare products and cosmetics. NADH is a raw healthcare product mainly used in anti-aging, treatment and prevention of chronic diseases, and other areas.

At present, NADH may be caused to degrade by various environmental factors due to its unstable chemical properties. The degradation is uneasy to be controlled in the conventional production process using ion exchange chromatography, causing that the purity of the final product is only about 90% and the yield is only 60%. Therefore, the production capability is greatly limited, and cannot meet the demand in the market.

Therefore, improvements and developments are needed in the art.

SUMMARY

Technical Problem

In view of the defects existing in the prior art, an object of the present invention is to provide a method for purifying reduced form of β-nicotinamide adenine dinucleotide, for the purpose of addressing the problems of low purity, low yield, and limited production capability occurring to a conventional process for purifying reduced form of β-nicotinamide adenine dinucleotide.

Technical Solution

To achieve the above object, the following technical solution is adopted in the present invention.

A method for purifying reduced form of β-nicotinamide adenine dinucleotide comprises the steps of a. sequentially microfiltrating and nanofiltrating a reaction solution obtained after an enzymatic reaction, to collect a concentrate for use;

b. then adding an ion pair reagent to the concentrate, and purifying by gradient elution using a reverse-phase chromatographic column as a stationary phase, a buffer solution as a phase A, and ethanol as a phase B;

c. changing the cations in the purified filtrate into sodium ions by using a cation exchange resin; and d. nanofiltrating the filtrate obtained in Step c, and finally freeze drying it in a vacuum freeze drier.

In the method for purifying reduced form of β-nicotinamide adenine dinucleotide, the nanofiltration membrane used for nanofiltration in Step a is a hollow fiber membrane with a 200 molecular weight cut-off.

In the method for purifying reduced form of β-nicotinamide adenine dinucleotide, the concentration of the concentrate in Step a is 30-40 g/L.

In the method for purifying reduced form of β-nicotinamide adenine dinucleotide, the ion pair reagent in Step b is tetramethylammonium hydroxide.

In the method for purifying reduced form of β-nicotinamide adenine dinucleotide, the reverse-phase chromatographic column in Step b is octylsilane-bonded silica gel.

In the method for purifying reduced form of β-nicotinamide adenine dinucleotide, the buffer solution in Step b is a 20 mM buffer solution formulated with hydrochloric acid and aqueous ammonia.

In the method for purifying reduced form of β-nicotinamide adenine dinucleotide, the buffer solution in Step b has a pH of 7-9.

In the method for purifying reduced form of β-nicotinamide adenine dinucleotide, the gradient elution time in Step b is 40 min.

In the method for purifying reduced form of β-nicotinamide adenine dinucleotide, the cation exchange resin in Step c is 001×7 strong cation exchange resin.

In the method for purifying reduced form of β-nicotinamide adenine dinucleotide, Step c specifically includes washing the cation exchange resin with 3 column volumes of hydrochloric acid, then with 3 column volumes of sodium hydroxide, and finally with pure water to give a pH of 7-8, loading the purified filtrate for salt change onto the cation exchange column, and collecting the eluate that is a product solution after salt change.

Beneficial Effect

In the method for purifying reduced form of β-nicotinamide adenine dinucleotide provided in the present invention, the reduced form of β-nicotinamide adenine dinucleotide is purified by reverse phase high performance liquid chromatography and cation exchange. As a result, the purity of the resulting product is up to 98%, the yield is up to 90% or more, and the production efficiency is 1 time higher than that of other processes, thus greatly reducing the production cost, and meeting the requirements for production and price in the market. Accordingly, the process has a broad application prospect.

DETAILED DESCRIPTION

The present invention provides a method for purifying reduced form of β-nicotinamide adenine dinucleotide. To make the objects, technical solutions, and effects of the present invention clearer and more precise, the present invention is described in further detail hereinafter. It should be understood that the specific embodiments described herein are merely provided for illustrating, instead of limiting the present invention.

The present invention provides a method for purifying reduced form of β-nicotinamide adenine dinucleotide, in which the reduced form of β-nicotinamide adenine dinucleotide is purified by reverse phase high performance liquid chromatography and cation exchange, such that the pufified reduced form of β-nicotinamide adenine dinucleotide has a high purity and high yield, thus meeting the requirements in industry.

A method for purifying reduced form of β-nicotinamide adenine dinucleotide comprises the steps of a. sequentially microfiltrating and nanofiltrating a reaction solution obtained after an enzymatic reaction, to collect a concentrate for use;

b. then adding an ion pair reagent to the concentrate, and purifying by gradient elution using a reverse-phase chromatographic column as a stationary phase, a buffer solution as a phase A, and ethanol as a phase B;

c. changing the cations in the purified filtrate into sodium ions by using a cation exchange resin; and d. nanofiltrating the filtrate obtained in Step c, and finally freeze drying it in a vacuum freeze drier.

In the present invention, the reaction solution obtained after an enzymatic reaction is firstly microfiltered in Step a, in which the microfiltration is carried out using a microfiltration membrane of 0.35 μm under an operation pressure of 0.1 Mpa, and the microfiltration is used to remove the microorganisms, because the microfiltration membrane allows macromolecules and dissolved inorganic salts to pass through, and retains microorganisms, bacteria, and suspended matter. Then, the filtrate obtained after microfiltration is nanofiltrated using a nanofiltration membrane, in which the nanofiltration membrane is a hollow fiber membrane, and preferably the nanofiltration membrane is a hollow fiber membrane with a 200 molecular weight cut-off. By using the nanofiltration membrane of this material, some dissolved salts and the organic compounds with a molecular weight of 200 or above can be removed, thereby further improving the purity and yield of the product.

In the present invention, the concentration of the concentrate in Step a is 30-40 g/L. In the present invention, the sample solution is treated by microfiltration and nanofiltration before injection, such that the particles, microorganisms, organic compounds and some dissolved inorganic salts are removed, to reduce the subsequent chromatographic elution time, and avoid the clogging of the column by particles, thereby extending the service life of the column. In the present invention, after concentration by microfiltration and nanofiltration in Step a, the concentration of the concentrate is 30-40 g/L. Concentrating the sample solution to such a concentration can facilitate the reduction of the sample elution time in Step b, and the improvement of the separation efficiency.

Preferably, in the present invention, the ion pair reagent in Step b is tetramethylammonium hydroxide. Where the retention time of the sample in the reverse-phase chromatographic column is short, a corresponding ion pair reagent may be added to bind the ions in the sample, thereby forming molecules that have retention on the column. The species of the ion pair reagent has a large influence on the separation effect. In the present invention, tetramethylammonium hydroxide is used as the ion pair reagent, which can effectively increase the retention time of the sample, improve the peak shape of a target shape, and lead to a most desirable separation effect.

In the present invention, the reverse-phase chromatographic column in Step b is octylsilane-bonded silica gel. By the mode of chromatographic separation in the present invention that the non-polar octylsilane-bonded silica gel is used as the stationary phase and the polar acidic aqueous ammonia is used as the mobile phase, the sample solution can be effectively separated, and the resulting reduced form of β-nicotinamide adenine dinucleotide has a high purity and a high yield.

In Step b in the present invention, the buffer solution is a 20 mM buffer solution formulated with hydrochloric acid and aqueous ammonia. The concentration of the buffer solution has a direct influence on the peak shape of a target component, thus affecting the separation effect of the chromatographic column. Where the concentration of the buffer solution is low, the chromatographic peak is caused to tail and broad. Where the concentration of the buffer solution is high, the chromatographic column is damaged, and the service life of the chromatographic column is shortened. In the present invention, when the concentration of the buffer solution is 20 mM, the peak shape of the resulting chromatographic peak is better, and the effect of chromatographic separation is more preferable.

Further, in Step b in the present invention, the buffer solution has a pH of 7-9. During the chromatographic analysis, if the material to be separated exists in a single form in the mobile phase, the full width at half maximum is small, the peak shape is symmetric, and the separation effect is much better. Where the pH of the buffer solution is 7-9, the resulting target peak has a good peak shape. Preferably, when the pH of the buffer solution is 8, the resulting target peak has a most desirable peak shape, and the separation effect is optimum.

Further, in Step b in the present invention, the volume ratio of the phase A to the phase B is greater than 4:96, and less than 1. Preferably, the volume ratio of the phase A to the phase B is greater than 30:70, and less than 40:60. In the range, the reduced form of β-nicotinamide adenine dinucleotide can be well separated.

Further, in Step b in the present invention, the gradient B % is from 4 to 14%. In such a range, the mobile phase can ensure that all the impurities can be eluted off, and the separation effect is good.

Further, in Step b in the present invention, the detection wavelength during the chromatographic analysis is 340 nm, because the reduced form of β-nicotinamide adenine dinucleotide has a maximum absorption at this wavelength. Therefore, the chromatographic peak has a good peak shape, and the sensitivity is high.

In Step b in the present invention, the gradient elution time is 40 min. Because the ingredients in the concentrate are complex, if isocratic elution is employed, the elution time is long, the separation efficiency is poor, and the sensitivity is less good. In the present invention, the reduced form of β-nicotinamide adenine dinucleotide is purified by gradient elution, such that the degree of separation is high, the separation time is short, the sensitivity is high, and the separation effect is good. The sample can be well separated when the gradient elution time is 40 min.

In the present invention, the cation exchange resin in Step c is 001×7 strong cation exchange resin characterized by rapid rate of exchange, high capacity of exchange, and high stablity, thus facilitating the change of the cations in the purified filtrate to sodium ions. The buffer solution in Step b is one formulated with hydrochloric acid and aqueous ammonia. The ammonium ions are the cations, and the ion pair reagent is also of cations.

In the present invention, Step c specifically comprises washing the cation exchange resin with 3 column volumes of hydrochloric acid, then with 3 column volumes of sodium hydroxide, and finally with pure water to give a pH of 7-8, loading the purified filtrate for salt change onto the cation exchange column, and collecting the eluate that is a product solution after salt change.

In Step d in the present invention, the product filtrate after salt change is concentrated to 100-150 g/L by nanofiltrating using a hollow fiber membrane with a 200 molecular weight cut-off, and then freeze dried in a vacuum freeze drier, to obtain a high-purity and high-yield freeze dried product.

The present invention is further described with reference to examples.

EXAMPLE 1

Sample treatment: A reaction solution obtained after an enzymatic reaction (for example, Lluis et al. (*biochimica et Biophysica Acta*, 480 (1997) 333-342)) was sequentially microfiltrated and nanofiltrated. The microfiltration was carried out using a microfiltration membrane of 0.35μm under an operation pressure of 0.1 Mpa, and the microfiltration was used to remove the microorganisms; and the nanofiltration was carried out using a hollow fiber membrane with a 200 molecular weight cut-off, to concentrate the filtrate to 3040 g/L. A concentrate was collected for use.

2. Purification:

Purification conditions: Chromatographic column: chromatographic column with octylsilane-bonded silica gel as a stationary phase, column diameter and length: 5 cm×30 cm; Mobile phases: Phase A: 20 mM buffer solution pH 7 formulated with hydrochloric acid and aqueous ammonia; Phase B: ethanol; Flow rate: 50-80 mL/min; Detection wavelength: 340 nm. Gradient: B %: 4%-14% (Elution time 40 min); Amount of injection: 10-15 g.

Purification process: 10 mM tetramethylammonium hydroxide was added to the concentrate, and the chromatographic column was rinsed with 30 wt % or above of ethanol, equilibrated, and loaded with the sample in an amount of 10-15 g sample filtrate. The sample was eluted for 40 min with a linear gradient, and the target peak was collect, which was held in a container and stored in a freezer at 2-8° C. for use.

3. Salt change: The 001×7 strong cation exchange resin was washed with 3 column volumes of 1 M hydrochloric acid, then with 3 column volumes of 0.5 M sodium hydroxide, and finally with pure water to give a pH of 7-8. The sample filtrate for salt change was loaded onto the cation exchange column, and the eluate was collected that was a product solution after salt change.

4. Concentration and freeze drying: The product solution after salt change was concentrated to 100-150 g/L by nanofiltrating using a nanofiltration membrane with a 200 molecular weight cut-off, and then freeze dried in a vacuum freeze drier, to obtain a freeze dried product with a purity that is higher than 98% and a total yield that can be up to 90.6%.

EXAMPLE 2

1. Sample treatment: A reaction solution obtained after an enzymatic reaction was sequentially microfiltrated and nanofiltrated. The microfiltration was carried out using a microfiltration membrane of 0.35 μm under an operation pressure of 0.1 Mpa, and the microfiltration was used to remove the microorganisms; and the nanofiltration was carried out using a hollow fiber membrane with a 200 molecular weight cut-off, to concentrate the filtrate to 30-40 g/L. A concentrate was collected for use.

2. Purification:

Purification conditions: Chromatographic column: chromatographic column with octylsilane-bonded silica gel as a stationary phase, column diameter and length: 15 cm×30 cm; Mobile phases: Phase A: 20 mM buffer solution pH 8 formulated with hydrochloric acid and aqueous ammonia; Phase B: ethanol; Flow rate: 400-500 mL/min; Detection wavelength: 340 nm. Gradient: B%: 4%-14% ((Elution time 40 min). Amount of injection: 80-100 g.

Purification process: 15 mM tetramethylammonium hydroxide was added to the concentrate, and the chromatographic column was rinsed with 30 wt % or above of ethanol, equilibrated, and loaded with the sample in an amount of 80-100 g sample filtrate. The sample was eluted for 40 min with a linear gradient, and the target peak was collect, which was held in a container and stored in a freezer at 2-8° C. for use.

3. Salt change: The 001×7 strong cation exchange resin was washed with 3 column volumes of 1 M hydrochloric acid, then with 3 column volumes of 0.5 M sodium hydroxide, and finally with pure water to give a pH of 7-8. The sample filtrate for salt change was loaded onto the cation exchange column, and the eluate was collected that was a product solution after salt change.

4. Concentration and freeze drying: The product solution after salt change was concentrated to 100-150 g/L by nanofiltrating using a nanofiltration membrane with a 200 molecular weight cut-off, and then freeze dried in a vacuum freeze drier, to obtain a freeze dried product with a purity that is higher than 98% and a total yield that can be up to 90.2%.

EXAMPLE 3

1. Sample treatment: A reaction solution obtained after an enzymatic reaction was sequentially microfiltrated and nanofiltrated. The microfiltration was carried out using a microfiltration membrane of 0.35 μm under an operation pressure of 0.1 Mpa, and the microfiltration was used to remove the microorganisms; and the nanofiltration was carried out using a hollow fiber membrane with a 200 molecular weight cut-off, to concentrate the filtrate to 30-40 g/L. A concentrate was collected for use.

2. Purification:

Purification conditions: Chromatographic column: chromatographic column with octylsilane-bonded silica gel as a stationary phase, column diameter and length: 30 cm×30 cm; Mobile phases: Phase A: 20 mM buffer solution pH 9 formulated with hydrochloric acid and aqueous ammonia; Phase B: ethanol; Flow rate: 2500-3000 mL/min; Detection wavelength: 340 nm. Gradient: B%: 4%-14% ((Elution time 40 min). Amount of injection: 400-500 g.

Purification process: 20 mM tetramethylammonium hydroxide was added to the concentrated sample solution, and the chromatographic column was rinsed with 30 wt % or above of ethanol, equilibrated, and loaded with the sample in an amount of 400-500 g sample filtrate. The sample was eluted for 40 min with a linear gradient, and the target peak was collect, which was held in a container and stored in a freezer at 2-8° C. for use.

3. Salt change: The 001×7 strong cation exchange resin was washed with 3 column volumes of 1 M hydrochloric acid, then with 3 column volumes of 0.5 M sodium hydroxide, and finally with pure water to give a pH of 7-8. The sample filtrate for salt change was loaded onto the cation exchange column, and the eluate was collected that was a product solution after salt change.

4. Concentration and freeze drying: The product solution after salt change was concentrated to 100-150 g/L by nanofiltrating using a nanofiltration membrane with a 200 molecular weight cut-off, and then freeze dried in a vacuum freeze drier, to obtain a freeze dried product with a purity that is higher than 98% and a total yield that can be up to 91.1%.

It can be known from the above examples that when the reverse phase high performance liquid chromatography and the cation exchange are used to purify the reduced form of β-nicotinamide adenine dinucleotide, the product obtained has a purity up to 98%, the yield is up to 90% or more, and the production efficiency is 1 time higher than that of other processes, thus greatly reducing the production cost, and meeting the requirements for production and price in the market. Accordingly, the process has a broad application prospect.

It should be understood that equivalent replacements or changes may be made by those ordinarily skilled in the art based on the technical solution and concept of the present invention, which are all embraced in the protection scope as defined by the accompanying claims of the present invention.

What is claimed is:

1. A method for purifying a salt of the reduced form of β-nicotinamide adenine dinucleotide (NADH), comprising:
    a. sequentially microfiltrating and nanofiltrating a crude solution containing NADH and NAD$^+$ to obtain a concentrate containing NADH and NAD$^+$;
    b. adding an ion pair reagent to the concentrate to obtain a loading sample, loading the loading sample onto a reverse-phase chromatographic column, and eluting the reverse chromatographic column with a gradient of a buffer solution as a phase A and ethanol as a phase B to obtain a purified NADH solution;
    c. changing cations in the purified NADH solution to sodium ions by a cation exchange resin to obtain a product solution; and
    d. nanofiltrating the product solution to obtain a concentrated product solution, and freeze drying the concentrated product solution in a vacuum freeze drier,
    wherein the ion pair reagent in step b is a tetramethylammonium hydroxide solution, the buffer solution in step b is a 20 mM buffer solution formulated with hydrochloric acid and aqueous ammonia at pH 7-9, and the ethanol is anhydrous ethanol.

2. The method for purifying a salt of the reduced form of β-nicotinamide adenine dinucleotide according to claim 1, wherein a nanofiltration membrane for the nanofiltrating in step a is a hollow fiber membrane with a 200 molecular weight cut-off.

3. The method for purifying a salt of the reduced form of β-nicotinamide adenine dinucleotide according to claim 1, wherein a concentration of the concentrate in step a is 30-40 g/L.

4. The method for purifying a salt of the reduced form of β-nicotinamide adenine dinucleotide according to claim 1, wherein the reverse-phase chromatographic column in step b includes octylsilane-bonded silica gel.

5. The method for purifying a salt of the reduced form of β-nicotinamide adenine dinucleotide according to claim 1, wherein the buffer solution in step b is a 20 mM buffer solution formulated with hydrochloric acid and aqueous ammonia.

6. The method for purifying a salt of the reduced form of β-nicotinamide adenine dinucleotide according to claim 1, wherein the buffer solution in step b has a pH of 7-9.

7. The method for purifying a salt of the reduced form of β-nicotinamide adenine dinucleotide according to claim 1, wherein an elution time for the eluting in step b is 40 min.

8. The method for purifying a salt of the reduced form of β-nicotinamide adenine dinucleotide according to claim 1, wherein the cation exchange resin in step c is 001 ×7 strong cation exchange resin.

9. The method for purifying a salt of the reduced form of β-nicotinamide adenine dinucleotide according to claim 8, wherein the step c further includes washing the cation exchange resin with 3 column volumes of hydrochloric acid, then with 3 column volumes of sodium hydroxide, and finally with pure water to give a pH of 7-8, loading the purified NADH solution onto the cation exchange column, and collecting an eluate that is the product solution after salt change.

10. The method for purifying a salt of the reduced form of β-nicotinamide adenine dinucleotide according to claim 1, wherein the step of changing the cations in step c includes washing the cation exchange resin with 3 column volumes of hydrochloric acid, then with 3 column volumes of sodium hydroxide, and finally with pure water to give a pH of 7-8, loading the purified NADH solution onto the cation exchange column, and collecting an eluate that is a product solution after salt change.

* * * * *